US010863952B2

(12) United States Patent
Vancamberg et al.

(10) Patent No.: US 10,863,952 B2
(45) Date of Patent: Dec. 15, 2020

(54) APPARATUS, SYSTEM AND METHOD FOR CONTROLLING MEDICAL EQUIPMENT

(71) Applicant: GENERAL ELECTRIC COMPANY, Schenectady, NY (US)

(72) Inventors: Laurence Vancamberg, Poissy (FR); Jérôme Sutty, Verrières le buisson (FR); Razvan Iordache, Paris (FR); Remy Klausz, Neuilly sur Seine (FR)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 124 days.

(21) Appl. No.: 16/014,752

(22) Filed: Jun. 21, 2018

(65) Prior Publication Data
US 2019/0388040 A1 Dec. 26, 2019

(51) Int. Cl.
A61B 6/04 (2006.01)
A61B 6/00 (2006.01)

(52) U.S. Cl.
CPC ............ *A61B 6/0414* (2013.01); *A61B 6/502* (2013.01); *A61B 6/0478* (2013.01); *A61B 6/52* (2013.01)

(58) Field of Classification Search
CPC ..... A61B 6/0414; A61B 6/502; A61B 6/0478; A61B 6/52
See application file for complete search history.

(56) References Cited

U.S. PATENT DOCUMENTS

| | | | | |
|---|---|---|---|---|
| 3,803,418 A | * | 4/1974 | Holstrom | A61B 6/0457 378/177 |
| 5,023,894 A | * | 6/1991 | Yamashita | A61B 5/1114 378/162 |
| 5,078,142 A | * | 1/1992 | Siczek | A61B 6/0435 600/407 |
| 5,289,520 A | * | 2/1994 | Pellegrino | A61B 6/0435 378/37 |
| 5,415,169 A | * | 5/1995 | Siczek | A61B 6/0435 600/427 |
| 5,590,166 A | | 12/1996 | Suni et al. | |
| 5,627,869 A | * | 5/1997 | Andrew | A61B 6/502 378/150 |
| 6,208,708 B1 | * | 3/2001 | Hoheisel | A61B 6/4233 250/370.09 |
| 6,298,114 B1 | * | 10/2001 | Yoda | A61B 6/0414 378/37 |
| 6,367,104 B1 | * | 4/2002 | Falbo, Sr. | A61B 6/0414 378/209 |
| 6,480,565 B1 | * | 11/2002 | Ning | A61B 6/032 378/20 |

(Continued)

FOREIGN PATENT DOCUMENTS

WO 2009114365 A2 9/2009
WO 2015079118 A1 6/2015

OTHER PUBLICATIONS

European application #19181561.2 filed Jun. 20, 2019; European Search Report dated Nov. 12, 2019; 6 pages.

*Primary Examiner* — Blake C Riddick
(74) *Attorney, Agent, or Firm* — Grogan, Tuccillo & Vanderleeden, LLP

(57) ABSTRACT

An apparatus for controlling medical equipment is provided. The apparatus includes patient positioning equipment, and a control system coupled to the patient positioning equipment. The control system is configured to control a function of the medical equipment.

20 Claims, 4 Drawing Sheets

(56) References Cited

U.S. PATENT DOCUMENTS

| | | | | |
|---|---|---|---|---|
| 6,483,891 B1* | 11/2002 | Lazarev | | A61B 6/0435 378/37 |
| 6,504,897 B1* | 1/2003 | Yonekawa | | A61B 6/00 378/57 |
| 6,640,364 B1* | 11/2003 | Josephson | | A61B 5/0555 378/209 |
| 7,613,276 B2 | 11/2009 | Sendai | | |
| 7,809,111 B2 | 10/2010 | Meer et al. | | |
| 8,159,370 B2 | 4/2012 | Shields et al. | | |
| 2002/0056160 A1* | 5/2002 | Falbo, Sr. | | A61B 6/0414 5/600 |
| 2002/0057758 A1* | 5/2002 | Stark | | A61B 6/502 378/37 |
| 2002/0122533 A1* | 9/2002 | Marie | | A61B 6/502 378/196 |
| 2003/0007598 A1* | 1/2003 | Wang | | A61B 8/5238 378/37 |
| 2003/0128033 A1* | 7/2003 | Sinkus | | A61B 5/0051 324/318 |
| 2004/0116914 A1* | 6/2004 | Dowlatshahi | | A61B 18/20 606/10 |
| 2007/0081625 A1* | 4/2007 | Sendai | | A61B 6/0414 378/37 |
| 2008/0043905 A1* | 2/2008 | Hassanpourgol | | A61B 6/0435 378/37 |
| 2008/0107234 A1* | 5/2008 | Amitani | | G01T 7/00 378/98.5 |
| 2008/0221478 A1* | 9/2008 | Ritchie | | A61B 6/0414 600/562 |
| 2009/0080604 A1* | 3/2009 | Shores | | A61B 10/0233 378/37 |
| 2009/0190715 A1* | 7/2009 | Meer | | A61B 6/467 378/37 |
| 2010/0123604 A1* | 5/2010 | Shields | | A61B 1/00016 341/20 |
| 2010/0290585 A1* | 11/2010 | Eliasson | | A61B 6/0435 378/37 |
| 2011/0073743 A1* | 3/2011 | Shamie | | B60R 11/02 248/537 |
| 2011/0087096 A1* | 4/2011 | Behar | | A61B 8/48 600/438 |
| 2011/0158383 A1* | 6/2011 | Ranjan | | A61B 6/0414 378/37 |
| 2012/0253187 A1* | 10/2012 | Hoernig | | A61B 6/0414 600/431 |
| 2013/0237859 A1* | 9/2013 | Taku | | A61B 5/708 600/476 |
| 2014/0058265 A1* | 2/2014 | Wang | | A61B 8/0825 600/447 |
| 2016/0183898 A1* | 6/2016 | Cormican | | A61B 6/0414 378/37 |
| 2016/0270751 A1* | 9/2016 | Laukkanen | | A61B 6/462 |
| 2016/0270764 A1* | 9/2016 | Wodecki | | A61B 8/462 |
| 2018/0280108 A1* | 10/2018 | Kevin | | A61B 10/0233 |

* cited by examiner

APPARATUS, SYSTEM AND METHOD FOR CONTROLLING MEDICAL EQUIPMENT

BACKGROUND

Technical Field

Embodiments of the invention relate generally to control systems for medical equipment, and more specifically, to an apparatus and method for the unified control of mammography equipment.

Discussion of Art

In the medical field, multiple pieces of mechanized equipment are often used in a medical procedure. For example, in the context of a mammogram, mammography equipment is typically coupled to patient positioning equipment, e.g., a moveable patient support table, which ensures proper positioning and support of a patient. As will be appreciated, during a mammogram, a practitioner must coordinate the movement of this equipment to obtain high quality mammographic images and/or biopsies.

More specifically, a practitioner must initiate movements of a mammographic gantry, as well as control breast compression, imaging parameters, and any other accessories employed during an examination. In addition to controlling the mammography equipment, a practitioner must adjust the patient positioning equipment so that the patient is in the correct angle and orientation necessary for the mammography imaging system or associated accessories to interface with the patient and function properly.

Typically, controls for mammography equipment are located on a gantry and/or main body of the equipment, as well as on one or more footswitch modules situated on the floor of the examination room. Given that such footswitches are on the floor, they may potentially contact or block the path of castors/wheels of the movable patent positioning system.

Moreover, controls on the various pieces of equipment utilized during a mammogram, i.e., controls for the mammography equipment and the patient positioning system, may be in potentially inconvenient locations relative to one another. That is, controls for the patient positioning system, e.g., controls that raise/lower or change the angle of a patient, are typically located on the positioning system. Controls for accessories are generally located on the accessories themselves, and, as mentioned, controls for the mammography equipment may be on the floor next to the equipment and on the gantry/body.

In addition, the various pieces of equipment are fabricated by different manufacturers and thus have no unified control system. As a result, the individual, equipment-specific controls must be utilized. To effectively use such controls, practitioners may have to reposition themselves multiple times during a procedure. Moreover, the practitioner often has both hands occupied, which potentially complicates effective equipment control.

What is needed, therefore, is an improved system and method for controlling medical equipment.

BRIEF SUMMARY OF THE INVENTION

In an embodiment, an apparatus for controlling medical equipment is provided. The apparatus includes patient positioning equipment, and a control system coupled to the patient positioning equipment. The control system is configured to control a function of the medical equipment.

In another embodiment, a system for controlling mammography equipment is provided. The system includes a mammography imaging system, a breast imaging table, and switch controls coupled to the breast imaging table. The switch controls are configured to control at least one function of the mammography equipment.

In yet another embodiment, a method of controlling medical equipment is provided. The method includes engaging a control system secured to patient positioning equipment, and controlling at least one function of the medical equipment via the control system.

BRIEF DESCRIPTION OF THE DRAWINGS

Features and advantages of embodiments of the present invention will become apparent on reading the detailed description below with reference to the drawings, which are illustrative but non-limiting, wherein.

DETAILED DESCRIPTION OF THE INVENTION

Figure 1:
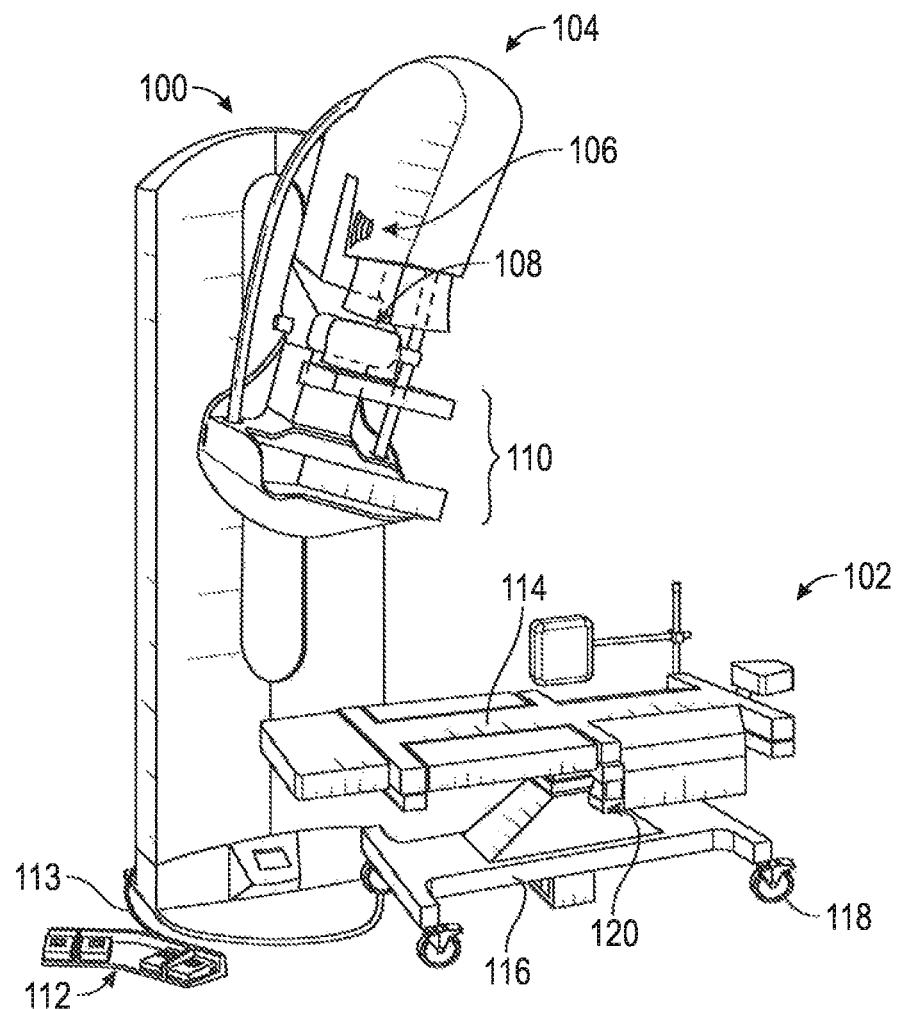
FIG. 1 illustrates an example of a common arrangement of a mammography imaging system and patient positioning equipment.

Reference will be made below in detail to exemplary embodiments of the invention, examples of which are illustrated in the accompanying drawings. Wherever possible, the same reference characters used throughout the drawings refer to the same or like parts, without duplicative description.

While embodiments disclosed herein are described with respect to a mammography imaging system and procedure, it is to be understood that embodiments of the present invention may be applicable to other types of diagnostic procedures and "medical equipment" generally, i.e., devices used by practitioners to perform a medical procedure, e.g., an x-ray, CT, ultrasound machine, biopsy machine, endoscope, cardiac catheter, fluoroscope, dental equipment, etc. More specifically, practitioners in the art will readily recognize that embodiments may be suitable for use with various diagnostic procedures that involve medical equipment and a patient positioning system. As will be appreciated, embodiments may be utilized for procedures on animals generally, and are not limited to human procedures.

As used herein, the terms "substantially," "generally," and "about" indicate conditions within reasonably achievable manufacturing and assembly tolerances, relative to ideal desired conditions suitable for achieving the functional purpose of a component or assembly.

Moreover, the term "patient positioning equipment", as used herein, refers to equipment that positions and/or supports a patient at the correct orientation necessary for the conduction of a procedure via medical equipment. As will be appreciated, the patient positioning equipment may be mechanized or manually configured and may include tables, chairs, support frames, kneelers, or other structures designed to position or support a patient during a medical procedure. In some embodiments, the patient positioning equipment is a decubitus mammography table/Decubitus Breast Imaging (DBI) table.

The term "control system", as used herein, refers a system for controlling one or more functions of medical equipment and/or patient positioning equipment and accessory equipment, and is not limited to a specific type of controller or interface. The term includes, but is not limited to, switch controls, i.e., a set of positionable operated controls, e.g., footswitch controls such as pedals, buttons, rocker switches, etc., that may be configurable to control the functions of medical equipment, patient positioning equipment, and/or accessory device actions. Control systems further include, but are not limited to, a user interface, i.e., a surface configured to receive inputs from a practitioner that translate to machine actions. The surface may contain multiple programmable switches or buttons, a tactile display surface, a touch pad, a display, or combinations thereof.

As used herein, the term "support structure" refers to a structure configured to interface with and support the switch controls and/or the user interface on the patient positioning equipment. This can include a rigid structure as well as a flexible mounts, e.g., a gooseneck mount. Also, as used herein, the terms "coupled" and "connect" mean to fasten or join as commonly used, and refers both to permanent affixation as well as selectively removable attachments. Typical connection/coupling devices/connectors/fasteners include fasteners, welds, clamps, straps, cables, zip ties, mating parts (e.g., post-socket, hinges, snap-fits, etc.), adhesives, friction fits, etc.

Turning now to FIG. 1, an example of a common arrangement of medical equipment 100, here a mammography imaging system/machine, paired with patient positioning equipment 102 is presented. The mammography imaging system 100 has a gantry 104 that contains side controls 106, front controls 108 above the compression paddle and breast support area 110, as well as switch controls 112, e.g., footswitch controls. Switch controls 112 are typically connected via a cable/wire 113 to mammography imaging system 100. The controls are also often mirrored on the opposite side of mammography imaging system 100 (not shown). As will be appreciated, other controls (not shown) may be present on particular accessories placed either in the paddle/breast support area 110, or added on to or integrated with the gantry 104.

As mentioned above, FIG. 1 further depicts patient positioning equipment 102, here a decubitus breast imaging table. The table 102 generally includes a support surface 114, e.g., a bed, mounted on a base 116, which is movable via wheels or casters 118. The support surface 114 may be rotatable/movable relative to the base 116. The table 102 has separate patient positioning controls 120 located on a side of the table 102 facing away from mammography imaging system 100.

In use, a practitioner must coordinate the functions of the mammography imaging system 100, the breast imaging table 102, and (optionally) any attached accessories. Functions of the mammography imaging system 100 include, but are not limited to, initiating movements of the mammographic gantry 104, including lift, rotation, and angulation. Further mammography imaging system functions include breast compression, imaging parameters (i.e., compression force, compression rate, field of view, lighting, radiation dosage, source angle), and, in in certain medical procedures, e.g., ultrasound-aided biopsies, needle movement, suction controls, and ultrasonic imaging parameters.

The table 102 includes multiple moving elements which guide and support a seated or reclined patient into the correct angle or orientation necessary for the mammography imaging system 100 and/or associated accessories to properly interface with the patient. Functions of the table 102 include raising or lowering a portion of the support surface 114 to, by way of non-limiting examples, change an angle of the surface 114 or adjust table height. These functions are manipulated through the use of controls 120 located on the table 102.

Moreover, accessories and tools, utilized for photographic imaging, volumetric measuring, tissue rigidity, and temperature mapping, may be employed during a mammographic examination. Accessory functions generally include powering the accessory and manipulating it to perform its intended task.

As discussed above, due to the locations of the aforementioned controls, as well as the lack of a unified control system, the path of the movable patent positioning system may be limited and/or blocked. Moreover, practitioners may have to reposition themselves multiple times during a procedure to access certain controls.

Figure 2:
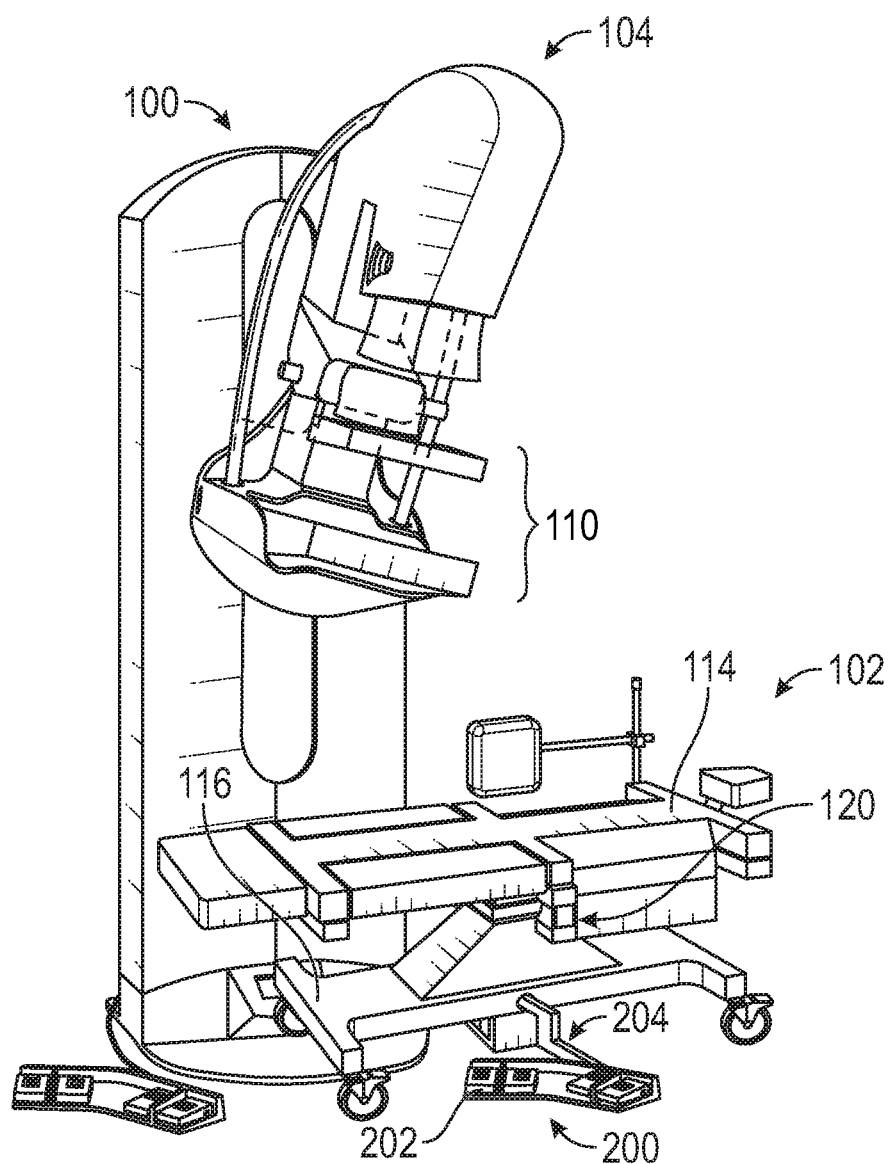
FIG. 2 illustrates an apparatus for controlling a mammography imaging system and patient positioning equipment according to an embodiment of the present invention.
Figure 3A:
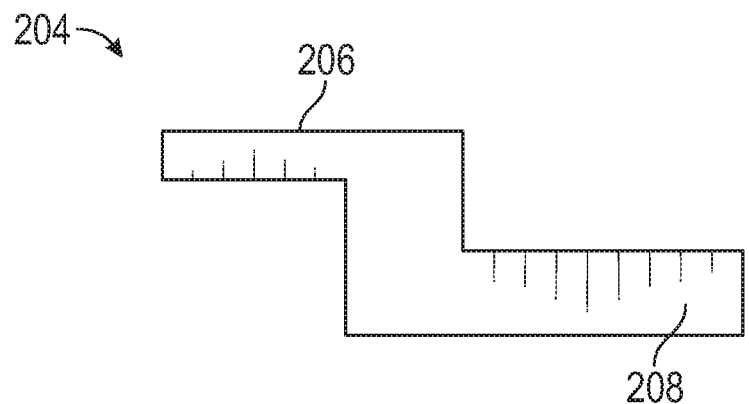
FIGS. 3A and 3B illustrate a support structure for use with an apparatus for controlling a mammography imaging system and patient positioning equipment according to an embodiment of the present invention.
Figure 3B:
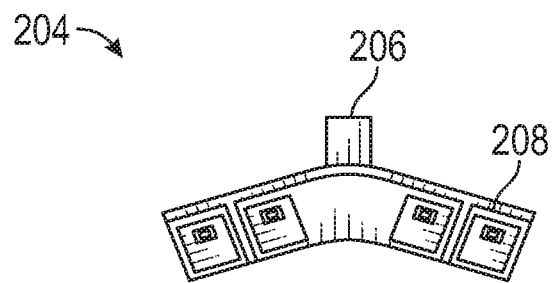

Turning now to FIG. 2, an embodiment of the inventive apparatus and system for controlling medical equipment is shown. In the embodiment, the control system 200 includes switch controls 202, e.g., a footswitch, that are connected to the table 102 by a support structure, e.g., brace 204. Referring to FIGS. 3A and 3B, in embodiments, the brace 204 includes a stepped arm portion 206 with a curved platform 208 configured to support auxiliary footswitch controls 200 (FIG. 2). The arm portion 206 may connect to the table 102 through a variety of devices including threaded apertures in the arm that allow fasteners to pass through and into apertures in the base 116 of the table 102. Although a mid-line installation next to patient position controls 120 is demonstrated, the switch controls 202 may be positioned at either end of the table 102 and may be fixed or movably mounted.

As will be appreciated, in certain embodiments, the support structure may be a structure other than the depicted brace 204, and the connection to the table 102 may be via a variety of attachment mechanisms. In certain embodiments, the support structure allows for the switch controls to be adjusted or moved, e.g., raised or lowered, relative to the base 116. In other embodiments, the switch controls may be integrated into/connected directly to the base 116, such that they do not require a separate support structure. Moreover, the switch controls 202 may be integrated with brace 204 to form a single movable piece.

The patient support table 102 may support multiple attachment points capable of accepting brace 204, including both on the table base 116 and on the support surface 114. In certain embodiments, the control system 200, e.g., footswitch controls 202, may be mirrored on the opposite side of the table 102. In other embodiments, multiple control systems 200 may be connected to the base 204 and/or the support surface 114. In embodiments, the control system 200 may be projected onto the floor/ground via an interactive projection system. In other words, the control system 200 may be a projection of a footswitch with one or more sensors, e.g., laser and/or cameras, detecting which part of the projected footswitch an operator is attempting to activate/interact with. As will be appreciated, projecting the control system 200 onto the ground increases the ease of mirroring the control system 200 on opposed sides of the table 102.

The control system 200 may communicate wirelessly (e.g., via wi-fi, Bluetooth, and/or a proprietary interface protocol) with the mammography imaging system 100 to control at least one function of the same. In other aspects, the control system 200 may be hardwired to the mammography imaging system 100.

In use, a practitioner/operator can manipulate the switch controls 202, e.g., footswitch, to control at least one function of the mammography imaging system 100, e.g., gantry lift, rotation, and angulation, while manipulating patient position controls 120 of the table 102 with one hand and supporting the patient with the other. In embodiments, the control system 200, e.g., footswitch controls 202, can be used to control a function of the patient positioning equipment and/or an accessory, in addition to controlling the mammography imaging system 100.

Figure 4:
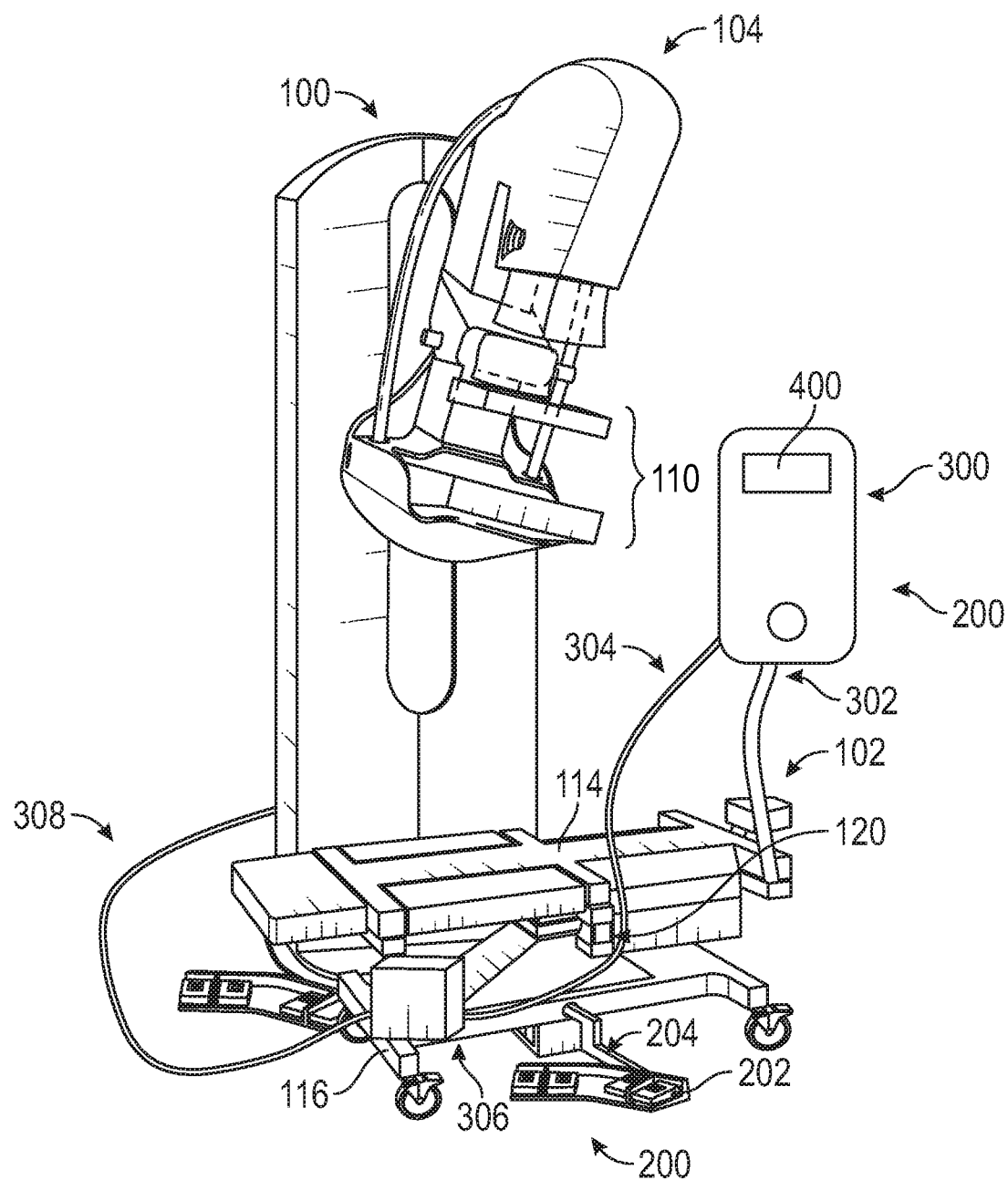
FIG. 4 illustrates an apparatus for controlling a mammography imaging system and patient positioning equipment according to another embodiment of the present invention.

Turning now to FIG. 4, the control system 200 can include a user interface 300. The user interface 300 can be in addition to, or in lieu of, switch controls 202. In embodiments, the switch controls 202 may be used to manipulate the user interface 300. The user interface 300 may be a touch screen device such as a tablet. In embodiments, the user interface 300 may be utilized to control at least one function of the mammography imaging system 100. The user interface 300 may also be utilized to control the table 102 and/or any accessory equipment, as well as the machine 100. In embodiments that do not include switch controls 202, the user interface 300 may be configured as a unified control system capable of controlling all associated equipment, e.g., machine 100, table 102 and any attached accessories. In embodiments, the user interface 300 may also display data obtained from mammography imaging system, or other equipment utilized during a procedure.

As depicted, the user interface 300 is mounted to patient support table 204 via a support structure, such as, for example, a flexible mount 302, e.g., a bendable gooseneck rod, such that the user interface 300 can be adjusted relative to a practitioner and the associated equipment. Alternatively, support structure may be rigid, such as a bracket.

A duplicate of the flexible mount 302 may also be attached to the medical equipment/mammography imaging system 100 to enable movement of user interface 300 from one piece of equipment to a second piece of equipment. For example, from patient support table 102 to mammography imaging system 100. Or, alternatively, the user interface 300 with support mount 302 may be moved from a first attachment point to a second attachment point. As will be appreciated, in embodiments, the table 102 may have a variety of attachment points for the support mount 302, on both the base 116 and support surface 114.

In embodiments, cables 304 and 308 link the user interface 300 to switch controls 202, a power/communications interface 306, and mammography imaging system 100. Cables 304 and 308 may carry power or data either singly or simultaneously and may be composed of single or multiple conductive elements. In other embodiments, cables may be eliminated altogether with communications provided via wireless signal such as wi-fi or Bluetooth protocols or with a proprietary interface protocol.

Interface 306 may perform the functions of power supply and communications regulation (i.e., command translation, analog to digital conversion, etc.) either singly or in tandem. In embodiments, the Interface 306 may include a rechargeable battery/power supply. Interface 306 further serves to receive commands from user interface 300 or auxiliary footswitch controls 200, interpret the commands, and output instructions triggering machine action in either the patient positioning equipment, the diagnostic equipment, or both. Power/communications interface 306 may include a stand-alone purpose-built device, a standard computer, or a computer containing additional hardware. Alternatively, the power/communications interface 306 may be integrated into the user interface 300, support mount 302, or brace 204. The power/communications interface 306 may be positioned in any location relative to the diagnostic and patient positioning equipment and other components of the modular control apparatus.

Thus, in use, a practitioner, in one instance, may engage switch controls 202 supported to initiate a movement of compression paddle, for example, after inputting target pressure into user interface 300 while supporting a patient on patient support table 114. In another instance, the practitioner may, after a first procedure, move user interface 300 to a second location, in order to perform a second procedure.

In embodiments, the switch controls 202 and/or user interface 300 controls can be configured such that when the patient positioning equipment, e.g., support table 114, is brought within a certain distance of the mammography imaging system, the controls are automatically activated to control functions of the mammography imaging system and/or accessories. As will be appreciated, the controls may also be user/practitioner activated.

Additionally, in embodiments, a control lock 400 may be disposed in the user interface 300 (as shown in FIG. 4), on the switch controls 202, table 102, and/or other suitable position. As will be understood, the control lock 400 restricts control of the function(s) of the medical equipment 100 and/or patient positioning equipment 102 so as to prevent unwanted/undesired activation of the medical equipment 100 and/or patient positioning equipment 102 via the control system 200. In embodiments, the control lock 400 includes a button or moveable switch that toggles the control lock 400 between a "locked" state, in which the control system 200 is prevented from activating the medical equipment 100 and/or the patient positioning equipment 102, and an "unlocked" state, in which the control system 200 is allowed to activate the medical equipment 100 and/or the patient positioning equipment 102. For example, in embodiments where the control lock 400 has a button, the control system 200 may be allowed to activate the medical equipment 100 and/or the patient positioning equipment 102 only while the button 400 is depressed. In other embodiments, in which the control lock 400 has a button, the control system 200 may be allowed to activate the medical equipment 100 and/or the patient positioning equipment 102 only for a predetermined amount of time after the button has been depressed. As will be appreciated, by restricting the ability of the control system 200 to activate the medical equipment 100 and/or the patient positioning equipment 102, the control lock 400 reduces the need to move the control system 200 to a designated holding position when the patient positioning equipment 102 is moved.

It is also to be understood that the medical equipment 100, the patient positioning equipment 102, and/or the control system 200 may include the necessary electronics, software, memory, storage, databases, firmware, logic/state machines, microprocessors, communication links, displays or other visual or audio user interfaces, printing devices, and any other input/output interfaces to perform the functions described herein and/or to achieve the results described herein. For example, the medical equipment 100, the patient positioning equipment 102, and/or the control system 200 may include at least one processor and system memory/data storage structures, which may include random access memory (RAM) and read-only memory (ROM). The at least one processor may include one or more conventional microprocessors and one or more supplementary co-processors such as math co-processors or the like. The data storage structures discussed herein may include an appropriate combination of magnetic, optical and/or semiconductor memory, and may include, for example, RAM, ROM, flash drive, an optical disc such as a compact disc and/or a hard disk or drive.

Additionally, a software application that adapts a controller to perform the methods disclosed herein may be read into a main memory of the at least one processor from a computer-readable medium. The term "computer-readable medium", as used herein, refers to any medium that provides or participates in providing instructions to the at least one processor of the medical equipment 100, the patient positioning equipment 102, and/or the control system 200 (or any other processor of a device described herein) for execution. Such a medium may take many forms, including but not limited to, non-volatile media and volatile media. Non-volatile media include, for example, optical, magnetic, or opto-magnetic disks, such as memory. Volatile media include dynamic random access memory (DRAM), which typically constitutes the main memory. Common forms of computer-readable media include, for example, a floppy disk, a flexible disk, hard disk, magnetic tape, any other magnetic medium, a CD-ROM, DVD, any other optical medium, a RAM, a PROM, an EPROM or EEPROM (electronically erasable programmable read-only memory), a FLASH-EEPROM, any other memory chip or cartridge, or any other medium from which a computer can read.

While in embodiments, the execution of sequences of instructions in the software application causes at least one processor to perform the methods/processes described herein, hard-wired circuitry may be used in place of, or in combination with, software instructions for implementation of the methods/processes of the present invention. Therefore, embodiments of the present invention are not limited to any specific combination of hardware and/or software.

It is further to be understood that the above description is intended to be illustrative, and not restrictive. For example, the above-described embodiments (and/or aspects thereof) may be used in combination with each other. Additionally, many modifications may be made to adapt a particular situation or material to the teachings of the invention without departing from its scope.

For example, in an embodiment, an apparatus for controlling medical equipment is provided. The apparatus includes patient positioning equipment, and a control system coupled to the patient positioning equipment. The control system is configured to control a function of the medical equipment. In certain embodiments, the control system includes switch controls connected to the patient positioning equipment via a support structure. In certain embodiments, the control system is configured to control a function of the patient positioning equipment and/or an accessory device, in addition to a function of the medical equipment. In certain embodiments, the medical equipment is a mammography imaging system. In certain embodiments, the patient positioning equipment is a breast imaging table. In certain embodiments, the breast imaging table is a Decubitus Breast Imaging (DBI) table. In certain embodiments, the control system is configured to support wireless communication with at least one of the medical equipment, the patient support equipment, or an accessory device. In certain embodiments, the control system is a user interface. In certain embodiments, the user interface is configured to control a function of the patient positioning equipment and/or an accessory device, in addition to a function of the medical equipment. In certain embodiments, the user interface is configured to support wireless communication with at least one of the medical equipment, the patient support equipment or an accessory device. In certain embodiments, the user interface is a touch screen. In certain embodiments, the user interface is coupled to the patient positioning equipment via a flexible mount.

Other embodiments provide for a system a system for controlling mammography equipment. The system includes a mammography imaging system, a breast imaging table, and switch controls coupled to the breast imaging table. The switch controls are configured to control at least one function of the mammography equipment. In certain embodiments, the switch controls are configured to control a function of the breast imaging table and/or an accessory device, in addition to a function of the mammography equipment. In certain embodiments, the system further includes a user interface coupled to the breast imaging table. The user interface is configured to control a function of the breast imaging table, a function of an accessory device, and/or a function of the mammography equipment.

Yet still other embodiments provide for a method of controlling medical equipment. The method includes engaging a control system secured to patient positioning equipment, and controlling at least one function of the medical equipment via the control system. In certain embodiments, the medical equipment is a mammography imaging system and the patient positioning equipment is a breast imaging table. In certain embodiments, the control system includes switch controls. In certain embodiments, the control system includes a user interface. In certain embodiments, the control system is configured to control a function of the patient positioning equipment and/or an accessory device, in addition to a function of the medical equipment.

Finally, the written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

Since certain changes may be made in the above-described invention, without departing from the spirit and scope of the invention herein involved, it is intended that all of the subject matter of the above description shown in the accompanying drawings shall be interpreted merely as examples illustrating the inventive concept herein and shall not be construed as limiting the invention.

What is claimed is:

1. A system for controlling medical equipment comprising:
   patient positioning equipment including at least a patient table;
   a mammography imaging system having a breast support area for compression of a breast of a patient with at least one compression paddle during an imaging procedure;
   a control device physically interconnected with the patient table of the patient positioning equipment and movable with the patient table, the control device being connected to the mammography imaging system only via a wire or wirelessly for controlling positioning of the at least one compression paddle;
   wherein the control device is configured to control both positioning of the patient table and positioning of the at least one compression paddle during the imaging procedure; and
   wherein the patient table and the mammography imaging system are mechanically separate.

2. The system of claim 1, wherein the control device includes switch controls connected to the patient positioning equipment via a support structure.

3. The system of claim 1, wherein the control device is configured to control a function of the patient positioning equipment and/or an accessory device, in addition to a function of the mammography imaging system.

4. The system of claim 1, wherein the patient table is a Decubitus Breast Imaging (DBI) table.

5. The system of claim 1, wherein the control device is configured to support wireless communication with at least one of the mammography imaging system, the patient positioning equipment, or an accessory device.

6. The system of claim 1, wherein the control device is a user interface.

7. The system of claim 6, wherein the user interface is configured to control a function of the patient positioning equipment and/or an accessory device, in addition to a function of the mammography imaging system.

8. The system of claim 6, wherein the user interface is configured to support wireless communication with at least one of the mammography imaging system, the patient positioning equipment or an accessory device.

9. The system of claim 6, wherein the user interface is a touch screen.

10. The apparatus of claim 6, wherein the user interface is coupled to the patient positioning equipment via a flexible mount.

11. The system of claim 1, wherein:
    the control device includes a footswitch controller.

12. The system of claim 1, further comprising:
    an accessory device configured to perform at least one of photographic imaging, volumetric measuring, tissue rigidity assessment and/or temperature mapping;
    wherein the control device is configured to control the accessory device to perform a function of the accessory device.

13. A system for controlling mammography equipment comprising:
    a mammography imaging system having a breast support area for compression of a breast of a patient with at least one compression paddle during an imaging procedure;
    a breast imaging table for supporting a patient during the imaging procedure, the breast imaging table having at least one wheel or caster for facilitating horizontal movement of the breast imaging table on a surface with respect to the mammography imaging system; and
    switch controls physically coupled to the breast imaging table and moveable therewith;
    wherein the switch controls are configured to control both positioning of the breast imaging table and positioning of the at least one compression paddle during the imaging procedure;
    wherein the breast imaging table is mechanically separate from, and moveable relative to, the mammography imaging system; and
    wherein the switch controls are connected to the mammography imaging system only via a wire or wirelessly for controlling positioning of the at least one compression paddle.

14. The system of claim 13, wherein the switch controls are configured to control a function of the breast imaging table and/or an accessory device, in addition to a function of the mammography imaging system.

15. The system of claim 14, further comprising:
    a user interface coupled to the breast imaging table, the user interface configured to control a function of the breast imaging table, a function of an accessory device, and/or a function of the mammography imaging system.

16. The system of claim 13, wherein:
    the switch controls are connected to the breast imaging table via a flexible gooseneck mount.

17. A method of controlling medical equipment comprising:
    physically interconnecting a controller to a patient positioning system having a patient table for supporting a patient;
    communicatively coupling the controller to the patient positioning system having a patient table for supporting a patient;
    communicatively coupling the controller to a mammography imaging system via only a wired or wireless connection, the mammography imaging system having a breast support area for compression of a breast of the patient with at least one compression paddle during an imaging procedure; and
    controlling at least one function of each of the patient table and the mammography imaging system using the controller;
    wherein the patient table and the mammography imaging system are mechanically separate.

18. The method of claim 17, wherein the controller includes switch controls.

19. The method of claim 17, wherein the controller includes a user interface.

20. The method of claim 17, wherein the controller is configured to control a function of the patient positioning system and/or an accessory device, in addition to a function of the mammography imaging system.

* * * * *